United States Patent [19]
Kroll

[11] Patent Number: 5,772,689
[45] Date of Patent: Jun. 30, 1998

[54] IMPLANTABLE CARDIOVERTER-DEFIBRILLATOR WITH APICAL SHOCK DELIVERY

[75] Inventor: Mark W. Kroll, Simi Valley, Calif.

[73] Assignee: Pacesetter, Inc., Sylmar, Calif.

[21] Appl. No.: 758,797

[22] Filed: Dec. 3, 1996

Related U.S. Application Data

[60] Provisional application No. 60/027,885 Jun. 28, 1996.
[51] Int. Cl.⁶ ................................................. A61N 1/39
[52] U.S. Cl. ................................................................ 607/4
[58] Field of Search .................................. 607/4, 15, 123, 607/63

[56] References Cited

U.S. PATENT DOCUMENTS

| | | | |
|---|---|---|---|
| 5,014,696 | 5/1991 | Mehra . | |
| 5,193,535 | 3/1993 | Bardy et al. . | |
| 5,325,870 | 7/1994 | Kroll et al. | 607/122 |
| 5,336,253 | 8/1994 | Gordon et al. | 607/122 |
| 5,342,414 | 8/1994 | Mehra | 607/127 |
| 5,431,681 | 7/1995 | Helland | 607/4 |

Primary Examiner—Scott M. Getzon

[57] ABSTRACT

An implantable electrical device comprising an RV coil and a pacing probe. The RV coil provides defibrillation and cardioversion waveforms to the heart and the pacing probe provides pacing signals to the heart and also acts as a sensor of the heart's intrinsic activity. The pacing probe is advantageously positioned within the apex of the heart. The device includes a controllable interconnect circuit that interconnects the RV coil and the pacing probe so that when the RV coil provides a defibrillation or cardioversion therapeutic shock to the heart, a portion of the energy provided to the RV coil is provided to the pacing probe so that an electrical shock is simultaneously provided to the apex for defibrillation or cardioversion purposes. In the preferred embodiment, a shunt resistor is positioned in series with the pacing probe so that the current being supplied to the pacing probe is limited. This protects the pacing probe from damage and also reduces the possibility that the cardiac cells surrounding the pacing probe will be stunned as a result of the pacing probe applying a therapeutic shock to the apex of the heart for defibrillation or cardioversion purposes.

38 Claims, 4 Drawing Sheets

IMPLANTABLE CARDIOVERTER-DEFIBRILLATOR WITH APICAL SHOCK DELIVERY

This application claims the benefit of U.S. Provisional Application No. 60/027,885 filing date Jun. 28, 1996

FIELD OF THE INVENTION

The present invention relates to implantable electrical devices that provide therapeutic shocks to the heart to regulate heart function and, more particularly, concerns an implantable cardioverter defibrillator that is capable of providing an improved defibrillation shock to the heart.

BACKGROUND OF THE INVENTION

Implantable electrical devices including implantable cardioverter-defibrillators (ICDs) and pacemakers are commonly used in medical practice to regulate heart function. These devices are implanted into the heart with one or more electrodes that are positioned within one or more chambers of the heart. When the heart is experiencing an arrhythmia, a control unit on the implantable electrical device is capable of sensing the arrhythmia and inducing an appropriately configured therapeutic shock to emanate from the electrodes into the heart to thereby desirably end the arrhythmia and restore normal heart function.

One type of arrhythmia that is particularly harmful to patients is ventricular fibrillation. Ventricular fibrillation is characterized by the seemingly random depolarization of individual fibers that comprise the ventricle of the heart. Ventricular fibrillation generally results in the ventricles of the heart pumping little, if any blood, which can very quickly result in the death of the victim.

An implantable electrical device can attempt to correct ventricular defibrillation by inducing a defibrillation pulse to emanate from one or more of the electrodes positioned within the heart. The defibrillation pulse is preferably configured to simultaneously stimulate a large portion of the individual fibers that comprise the ventricles to thereby allow simultaneous repolarization of these nerve fibers. Subsequently, the nerve fibers will then preferably depolarize and repolarize in a more normal fashion.

One difficulty with the implantable electrical devices that provide defibrillation shocks is that these shocks generally require a significant amount of energy. In particular, the shock must deliver a sufficient amount of current to the heart so that a significant portion of the nerve cells of the heart are stimulated. With most implantable electrical devices, however, the power supply is generally comprised of a battery and repeated defibrillation shocks can ultimately deplete the battery to the point where the implantable electrical device is not operable. Hence, there has always been a strong desire to design implantable electrical devices so that the threshold value of energy emanating from the electrodes is reduced as much as possible while still being sufficient to result in successful ventricular defibrillation. This also reduces the size of the implantable electrical device.

Various approaches have been taken in order to result in more efficient defibrillation of the heart. For example, U.S. Pat. No. 4,953,551 to Mehra et al. discloses a system for defibrillating a heart wherein there are electrodes that are positioned within the chambers of the heart, the superior vena cava and also outside of the heart. The combination of these electrodes are then used to induce a biphasic current waveform which is relatively efficient at defibrillating the heart. It is understood that one particularly advantageous place to position an electrode to stimulate the heart is within the apex of the ventricle of the heart. Shocks delivered from this location are particularly efficient at inducing defibrillation of the heart. While Mehra et al. advantageously positions an electrode in the apex of the heart, it is understood that in many applications it is not possible to position a defibrillation electrode in the apex of the heart.

In particular, many common implantable electrical devices perform both a defibrillation and a cardioversion function and a pacing function. Generally, the pacing electrode is positioned in the apex of the heart so that a low voltage signal can be applied at the most sensitive region of the heart to provide pacing to the heart. Consequently, it is often not possible to position a defibrillation electrode at this position in the ventricle of the heart even though an electrode in this position would be more efficient at providing defibrillation and cardioversions shocks to the heart.

Further, it is generally not possible to use the pacing probe for defibrillation or cardioversion purposes as large amounts of current provided to the pacing electrode can result in a number of serious consequences. First, the wiring that is used in the pacing connection can be damaged or destroyed as a result of applying too much current. Further, even with moderate shock currents, the pacing tip can be polarized and the region of heart cells near the pacing tip can be stunned. When these cells are stunned the pacing tip cannot perform the function of sensing the function of the heart. It is understood that the pacing tip in implantable electrical devices is often used to provide signals to the controller as to the functioning of the heart. If the cells located adjacent the pacing tip are stunned, then the controller will not receive any information indicative of the performance of the heart during the critical interval following the delivery of a defibrillation or cardioversion pulse.

Hence, there is a need for an implantable electrical device that is capable of providing pacing pulses and cardioversion and defibrillation shocks to the heart that uses less energy to achieve successful cardioversion and defibrillation to thereby increase the longevity of the system. To this end, there is a need for a system that is capable of providing both pacing pulses and cardioversion and defibrillation pulses from an electrode located substantially adjacent the apex of the ventricle of the heart while reducing the risk of damage to the electrode positioned in the apex or the surrounding cardiac cells in the apex.

SUMMARY OF THE INVENTION

The aforementioned needs are satisfied by the present invention which is comprised of an implantable electrical device that has a first electrode positioned substantially adjacent the apex of the heart and a second electrode positioned within the ventricle of the heart wherein the first electrode is configured to be able to provide pacing pulses to the heart and the second electrode is configured to provide cardioversion and defibrillation pulses to the heart. The implantable electrical device is also configured so that when a cardioversion or defibrillation pulse is provided to the heart via the second electrode, a portion of the pulse is also provided via the first electrode to the apex of the heart. In the preferred embodiment, the implantable electrical device includes circuitry which limits the amount of current that is provided to the first electrode when a cardioversion or defibrillation pulse is being applied to the heart.

The system of the preferred embodiment provides for more efficient defibrillation by applying a current limited defibrillation or cardioversion shock to the apex of the heart simultaneously with a defibrillation or cardioversion shock that is provided to the ventricle. In the preferred embodiment, the circuitry that interconnects the second electrode and the first electrode and provides the shock to the apex of the heart limits the amount of current that is supplied to the apex of the heart to avoid damage to the pacing tip and also to avoid stunning the tissue surrounding the apex of the heart.

Consequently, the system of the preferred embodiment is configured to be able to provide a more efficient defibrillation and cardioversion shock, thereby lowering the threshold energy value of the shock, without significantly diminishing the heart function sensing capability of the pacing tip. These and other objects and advantages of the present invention will become more fully apparent from the following description taken in conjunction with the accompanying drawings.

DETAILED DESCRIPTION OF THE PREFERRED EMBODIMENT

Figure 1:
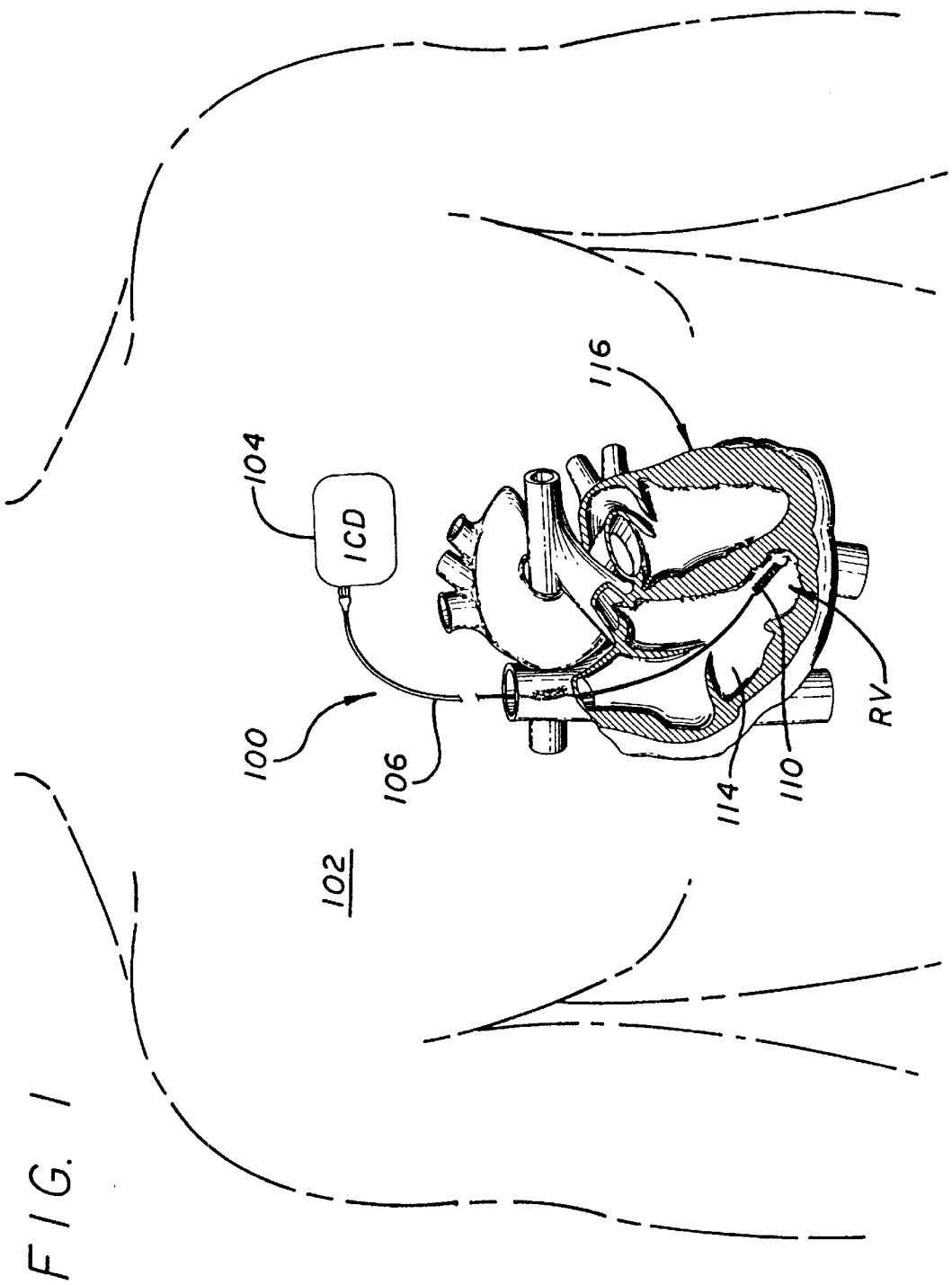
FIG. 1 is a schematic illustration of an implantable electrical device of the preferred embodiment that is configured to regulate the function of a heart of a patient.
Figure 2:
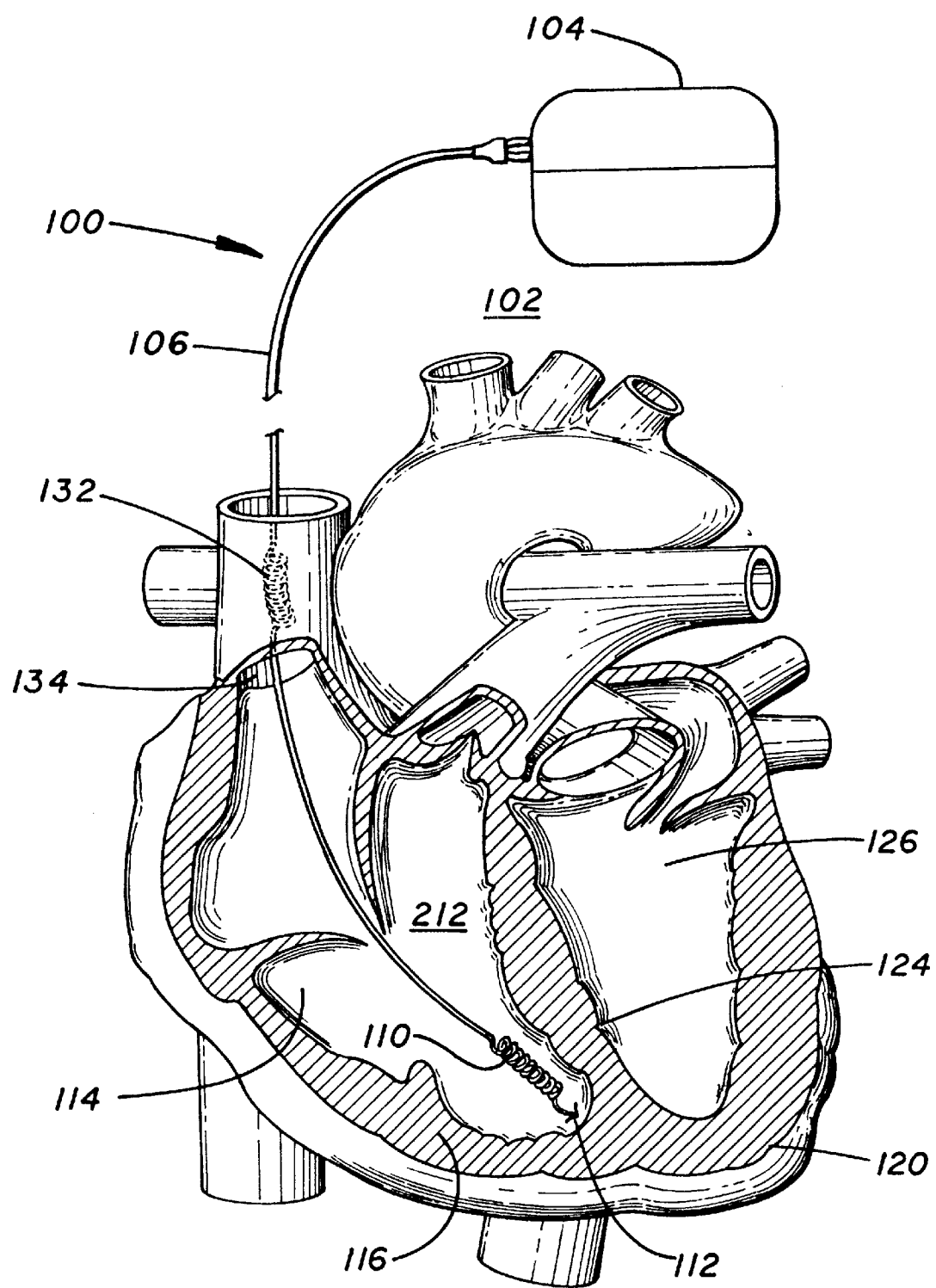
FIG. 2 is a detailed schematic view of the implantable electrical device of FIG. 1.

Reference will now be made to the drawings wherein like numerals refer to like parts throughout. FIGS. 1 and 2 illustrate an implantable electrical device 100 that is implanted within the body of a patient 102. In this embodiment, the implantable electrical device 100 is comprised of an implantable cardioverter-defibrillator (ICD) that includes a casing 104 that is connected via one or more leads 106 to an RV coil electrode 110 and a pacing tip 112.

The RV coil 110 and the pacing tip 112 are preferably positioned within a right ventricle 114 of the patient's heart 116. In particular, the pacing tip 112 is positioned in direct contact with the inner wall of the right ventricle 114 at a position adjacent the apex 120 of the heart 116. As is understood, positioning the pacing tip 112 in the location adjacent the apex 120 of the heart 116 facilitates regulating the function of the heart 116 via low voltage (e.g. 5 volts or less) pacing pulses.

In operation, the implantable electrical device 100 of the preferred embodiment includes a controller 130 (FIG. 3) that is positioned within the casing 104.

The controller 130 receives a sense signal from the pacing tip 112 which is indicative of the intrinsic function of the heart 116. The pacing tip 112 is configured to sense the activity of the heart 116 and provide a sense signal input 129 indicative thereof to the controller 130 so that the controller can induce the application of appropriate electrical stimuli to the heart 116 via either the RV coil 110 or the pacing tip 112 to regulate or correct abnormal intrinsic heart function.

In particular, when the controller 130 receives a signal indicating that the heart 116 is experiencing a form of arrhythmia that can be corrected via a low voltage pacing pulse, the pulse is provided at an appropriate interval via the pacing tip 112. Similarly, when the controller 130 receives a signal indicating that the heart 116 is experiencing a more significant problem such as ventricular defibrillation or ventricular tachycardia, the controller 130 then induces the RV coil 110 to provide a therapeutic shock to the heart 116.

In the embodiment shown in FIG. 1, the implantable electrical device 100 is comprised of a unipolar pectoral implant ICD. In this embodiment, the casing 104 provides the return electrode for the electrical shock that emanates from the RV coil 110. The RV coil 110 is typically positioned adjacent the right ventricular freewall so that the current emanating from the RV coil 110 passes through the right ventricle 114 of the heart to the septum 124 and then to the left ventricle 126 of the heart and then outward to the casing 104. Preferably, the waveform that is being applied via the RV coil 110 is configured to induce the heart 106 to return to a normal sinus rhythm.

It is understood that a pectoral implant unipolar ICD is more efficient than other prior art ICD's at restoring the heart to a normal sinus rhythm and therefore the threshold energy value of the waveform that emanates from the RV coil 110 of the device of the preferred embodiment is lower than the devices of the prior art. It will be appreciated, however, that a superior vena cava electrode 132 can be positioned within the superior vena cava 134 of the heart to provide the return electrode for the implantable electrical device 100 when a cardioversion or defibrillation waveform is provided to the heart 116 from the RV coil 110.

In the embodiment shown in FIGS. 1 and 2, the implantable electrical device 100 is configured so that, when a cardioversion or defibrillation waveform emanates from the coil 110, a waveform is also simultaneously applied to the apex 120 of the heart 116 via the pacing tip 112. As is discussed hereinbelow, the implantable electrical device 100 is configured so that the therapeutic shock that is provided to the apex 120 of the heart via the pacing tip 112 is configured so as to limit the amount of current that is provided to the apex 120 via the pacing tip 112. This reduces the likelihood that the pacing tip 112 will be damaged and that the cardiac cells located adjacent the pacing tip 112 will be stunned or damaged during application of the waveform.

Figure 3:
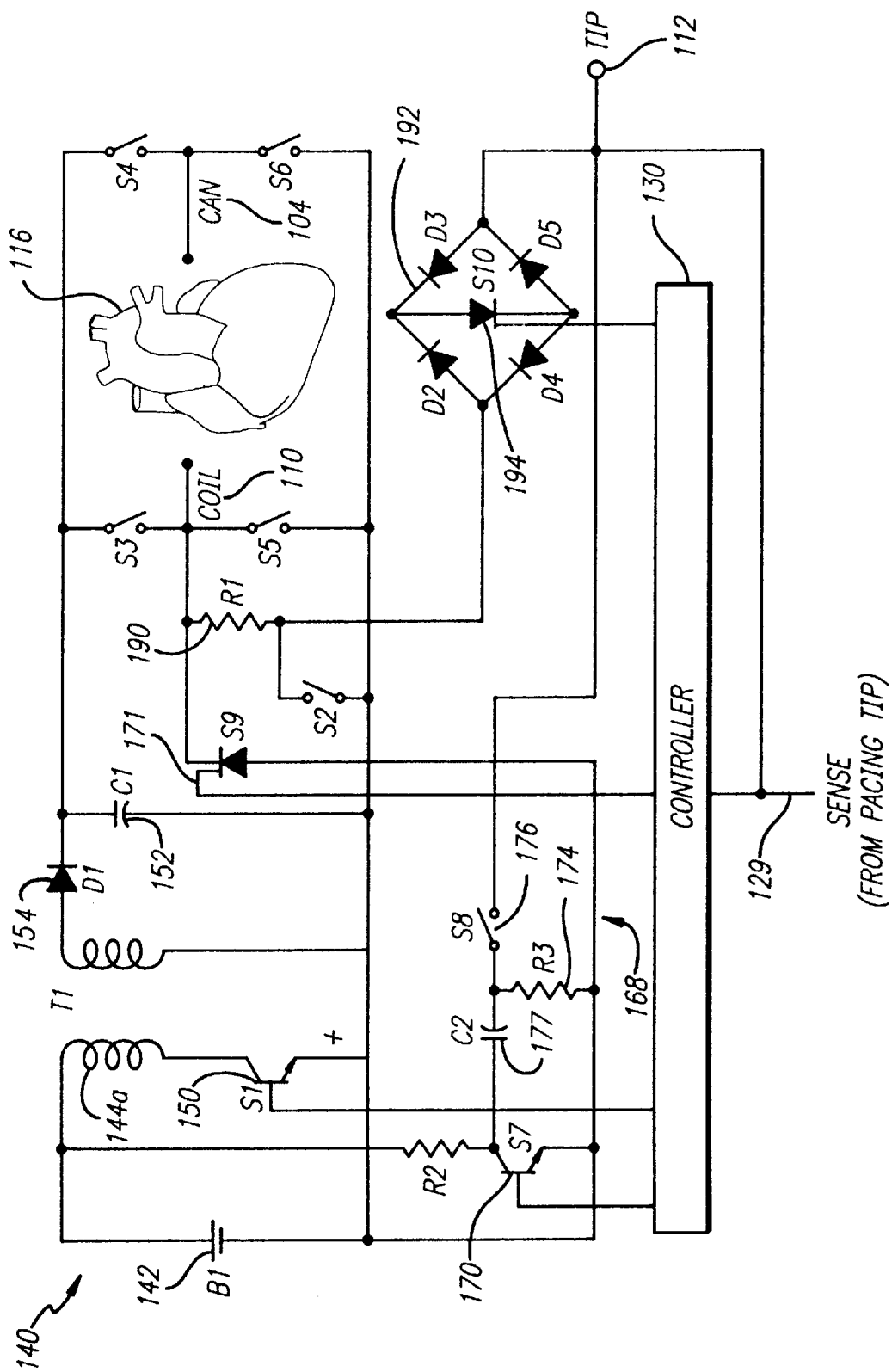
FIG. 3 is an electrical schematic that illustrates a preferred embodiment of a implantable cardioverter defibrillator that provides an apical shock through a pacing tip.

Referring now to FIG. 3, the exact configuration of the circuitry of the implantable electrical device 100 of the preferred embodiment is shown. In particular, FIG. 3 illustrates that the implantable electrical device 100 includes the controller 130 that controls a plurality of switches within an electrical circuit 140. The circuit 140 includes a power supply 142 which is designated as a battery B1. The battery B1 provides a voltage to a primary winding 144a of a transformer 146 in response to the controller 130 inducing a transistor 150, designated switch S1, to be closed. This results in the secondary winding 144b of the transformer 146 being energized and charging a capacitor 152, designated C1, through a diode 154 designated D1. Hence, the controller 130 can charge the capacitor C1 so that the voltage stored on the capacitor C1 can be applied to the heart 116 via manipulation of four switches S3–S6 that form an H-bridge 156.

Figure 4:
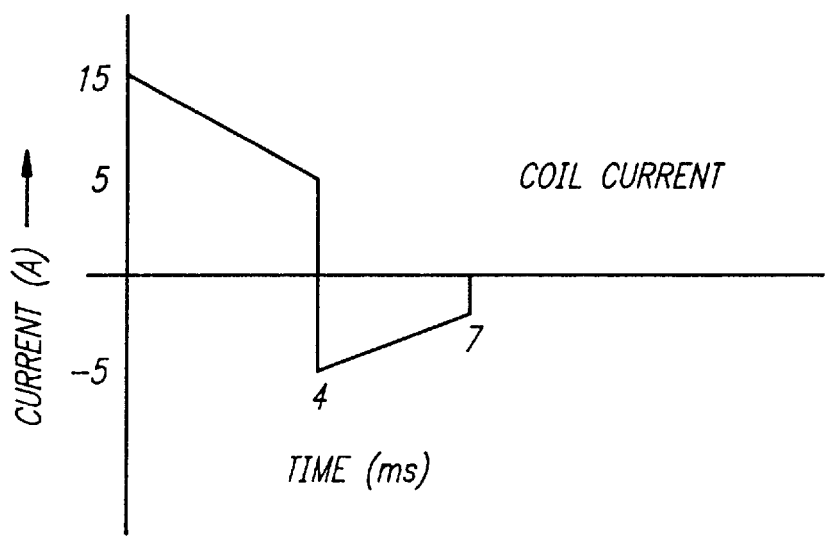
FIG. 4 is a diagram which illustrates an exemplary current waveform provided via the RV coil of the implantable electrical device of FIG. 1.

As shown in FIG. 3, the therapeutic shock is provided from the coil 110 to the heart 116 and then the can 104 (FIG. 1) provides the return electrode for the applied waveform. Generally, the switches S3 and S6 are initially closed to provide a waveform to the heart 116 that has a voltage of approximately 750 volts at the leading edge. As the resistance between the can 104 and the coil 110 is approximately 50 Ohms, the current at the leading edge is approximately 15A as indicated by FIG. 4. This voltage then exponentially decays for approximately 3 milliseconds until the switches S4 and S5 of the H-bridge 156 are closed and the switches S3 and S6 are opened in response to signals from the controller 130. This results in a negative voltage of approximately −250 volts (or approximately −5 amperes) being applied to the heart which then exponentially decays to approximately −100 volts at which time the switches S4 and S5 are disabled. In this fashion, a bipolar defibrillation waveform can be applied to the heart 116 for therapeutic purposes. The operation of the circuit 140 in applying a bipolar defibrillation waveform is consistent with the operation of ICD devices of the prior art.

Similarly, the circuit 140 is also capable of providing pacing pulses or shocks via a pacing circuit 168 and the pacing probe or tip 112 to the heart 116 in the following manner. The battery 142 is connected to a transistor switch 170 designated as S7 via a resistor 172 designated R2. The base of the transistor switch 170 is controlled via the controller 130 and when the switch 170 is activated a pulse can then be transmitted to the tip 112 via a capacitor 172 and a resistor 174, designated C2 and R3 respectively, to the tip 112 when a switch 180 designated S8 is closed by the controller 130. Specifically, the switch S7 is activated with the switch S8 opened so as to charge the capacitor C2 to a desired level through resistors R2 and R3. Subsequently, the switch S8 is closed to provide the pacing pulse to the tip 112.

Advantageously, the RV coil 110 positioned within the right ventricle functions as the return electrode for the pacing pulse in this embodiment. In particular, when a pacing pulse is provided to the heart 116, the controller 130 induces an SCR switch 171, designated S9, to close thereby connecting to the coil 110. This results in the RV coil 110 acting as the return for the pacing pulse. The operation and function of the pacing circuit 168 is similar to the operation and function of pacing circuits of the prior art.

Hence, the implantable electrical device 100 of the preferred embodiment is capable of providing both cardioversion-defibrillation therapeutic waveforms and pacing pulses. Further, the implantable electrical device 100 is also capable of using the pacing probe 112 to provide a cardioversion or defibrillation pulse directly to the apex 120 of the heart 116. In particular, the circuit 140 includes a dump resistor 190, designated R1, that is connected between the coil 110 and a diode bridge circuit 192. The dump resistor 190 is used both for the purposes described hereinbelow and is also used to dissipate excess charge stored in the capacitor C1, for reasons that are readily understood in the art, by the controller 130 closing a switch S2. The diode bridge circuit 192 is comprised of four diodes D2 through D5 with a switch S10 interposed between the cathodes of D4 and D5 and the anodes of D2 and D3. The pacing tip 112 is connected to the diode bridge 192 at a point between the anode of D5 and the cathode of D3.

The controller 130 and the circuit 140 operate in the following manner to provide a cardioversion or defibrillation shock to the heart 116 with a portion being directed via the tip 112 to the apex 120 of the heart 116. Specifically, the controller 130 induces the switches S3 through S6, comprising the H-bridge 156, to open and close in the above-described manner to provide the biphasic shock to the heart 116. Further, the controller 130 sends a signal to the switch S10, so as to enable the switch S10.

Figure 5:
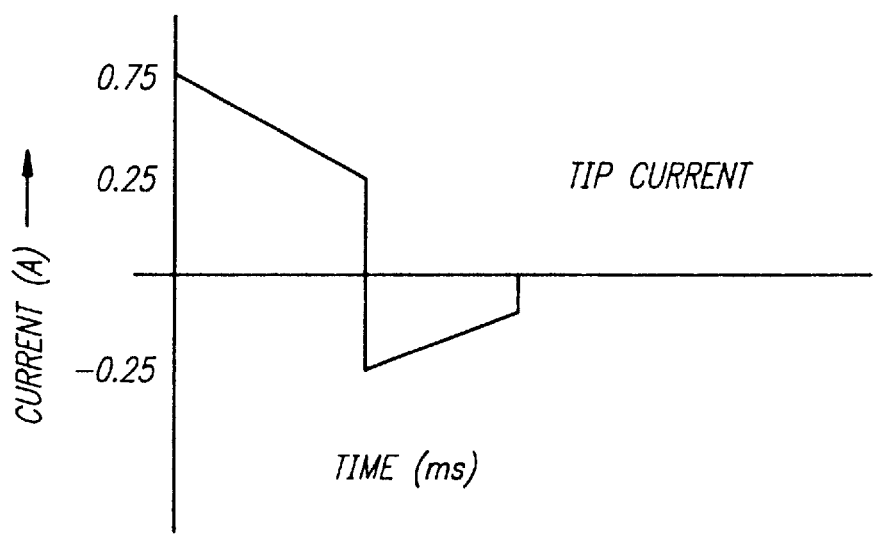
FIG. 5 is a diagram which illustrates an exemplary current waveform of the therapeutic shock that is delivered via the pacing tip to the apex of the heart using the implantable electrical device of FIG. 1.

FIG. 4 illustrates the current waveform that is being applied to the heart 116 between the coil 110 and the casing 104 (FIGS. 1 and 2) and FIG. 5 illustrates the current waveform that is being applied to the apex 120 of the heart 116 via the pacing tip 112. As shown, both of these waveforms are biphasic, i.e., have a positive portion and a negative portion.

When the positive portion of the biphasic waveform of FIG. 4 is applied to the heart 116 via the H-bridge 156, a portion of the current is directed from the coil 110 through the resistor 190 to the diode bridge 192. The positive portion of the shock flows through steering diode D2, switch S10 and finally steering diode D5 to the tip 112. Similarly, during the negative phase of the shock, the current flows from the coil 110 through the resistor R1 into the diode bridge 192. In the diode bridge, the current flows through the steering diode D4, the switch S10 and finally the steering diode D3 to the tip 112. Consequently, the waveform of the current that is provided through the tip 112 has the same general shape as the waveform of the current that is being applied from the coil 110 except that the current is reduced by the resistor R1. Switches 171 (S9) and 194 (S10) show a simplified direct gate connector which would actually be made through some sort of transformer or optical isolation.

In one preferred embodiment, the resistor R1 is a dump resistor that has a 500 ohm value. Further, the pacing tip 112 has a resistance of approximately 500 ohms as well (into the heart). Consequently, the current that is being supplied via the pacing tip to the apex 120 of the heart is limited to approximately 0.75A when 15A of current is supplied via the coil 110 to the heart 116. Similarly, −0.25A of current is applied via the pacing tip 112 to the apex 120 of the heart 116 when approximately −5A is applied from the coil 110 to the heart 116.

It will be appreciated that the circuit 140 is configured to apply a low current pulse to the apex 120 of the heart 116 while simultaneously applying a significantly higher amplitude cardioversion or defibrillation waveform to the ventricle walls of the heart 116. Using the dump resistor 190 results in the current that is applied to the apex 120 of the heart 116 being limited to such an extent that the pacing tip 112 is protected and also so that the cardiac cells surrounding the pacing tip are not stunned or otherwise damaged by application of the cardioversion or defibrillation shock to the apex of the heart. Consequently, a more efficient field can be applied to the heart thereby reducing the overall threshold of energy that has to be applied to the heart to achieve cardioversion or defibrillation. This results in an improved efficiency in cardioversion and defibrillation and also results in less depletion of the battery thereby extending the life of the device. It will be appreciated that the dump resistor is but one of many ways of limiting the current that is being applied to the apex of the heart.

Although the foregoing description of the preferred embodiment of the present invention has shown, described and pointed out the fundamental novel features of the invention, it will be understood that various omissions, substitutions, and changes in the form of the detail of the apparatus as illustrated as well as the uses thereof, may be made by those skilled in the art without departing from the spirit of the present invention. Consequently, the scope of the invention should not be limited to the foregoing discussion, but should be defined by the appended claims.

What is claimed is:

1. An implantable electrical device for applying a therapeutic stimulation pulse to a heart of a patient comprising:

first electrode adapted to be positioned within a ventricle of the heart in a first position and configured to provide a first therapeutic stimulation pulse to the heart wherein the first therapeutic stimulation pulse is configured to be provided for defibrillation or cardioversion purposes;

a second electrode adapted to be positioned within the ventricle of the heart in a second position wherein the second electrode is further configured to provide pacing pulses to a second region of the heart adjacent the second position;

a current limiting circuit being configured so that, when the first electrode is providing the first therapeutic stimulation pulse to the heart, the second electrode provides an additional therapeutic stimulation pulse to the second region of the heart for cardioversion or defibrillation purposes wherein the circuit includes a means for limiting the current provided by the second electrode to the second region during delivery of the additional stimulation pulse; and a controller that provides therapeutic stimulation pulses to the heart via the first and second electrodes and wherein the controller enables the current limiting means when providing the first therapeutic stimulation pulse to the heart and wherein the current limiting means is disabled during delivery of pacing pulses to the second region of the heart via the second electrode.

2. The device of claim 1, wherein the controller receives an input signal indicative of the function of the heart and wherein the controller induces the first or second electrode to provide a cardioversion or defibrillation shock or a pacing pulse to the heart based upon the input signal.

3. The device of claim 2, wherein the second electrode is comprised of a pacing probe that is implanted into the heart tissue in an apex region of the heart.

4. The device of claim 3, wherein the current limiting circuit is comprised of a plurality of controllable switches that are configurable in response to signals from the controller.

5. The device of claim 3, wherein the current limiting means is comprised of a resistor that is connected in series between the first and second electrode so that the portion of energy that is transmitted to the second electrode by the current limiting circuit is current limited so that the likelihood of damage to the pacing probe and the likelihood of stunning the cardiac cells positioned adjacent the pacing probe is reduced.

6. The device of claim 5, wherein the resistor is comprised of a dump resistor that the current limiting circuit, in a first configuration, uses to dissipate excess energy and wherein the current limiting circuit, in a second configuration, uses the dump resistor to limit the amount of current being provided to the pacing probe.

7. The device of claim 6, wherein the current limiting circuit is configured to apply a biphasic defibrillation shock to the heart via the first electrode and wherein the controllable circuit includes a diode bridge interposed between the resistor and the second electrode so that the circuit is configured to apply a current limited biphasic shock to the apex of the heart via the second electrode.

8. The device of claim 7, wherein the peak positive current provided to the heart via the first electrode is approximately 15 amperes and the peak negative current provided to the heart via the first electrode is approximately −5 amperes and wherein the resistor limits the peak current provided by the second electrode to approximately 0.75 amperes and the peak negative current provided to the heart to approximately −0.25 amperes.

9. The device of claim 8, wherein the controller is positioned within a can that is adapted to be implanted within the body of the patient and wherein the can is implanted in the patient's body adjacent the heart and wherein the can is configured to provide the return electrode for the heart when the defibrillation stimulation pulse is applied to the heart from the first electrode.

10. The device of claim 9, wherein the controllable circuit is configurable so that the first electrode provides the return electrode for the pacing pulse applied to the apex of the heart from the second electrode.

11. An implantable electrical device for applying therapeutic pulses to the heart of a patient, the device comprising:

first means adapted to be implanted in the ventricle of the heart for providing a first therapeutic stimulation pulse to the heart for cardioversion or defibrillation purposes;

second means adapted to be implanted in the ventricle of the heart for providing a second therapeutic stimulation pulse to a first region of the heart for pacing purposes;

interconnect means for interconnecting the first and second means so that when the first means is providing the first therapeutic stimulation pulse to the heart, the second means simultaneously provides a therapeutic stimulation pulse to the first region of the heart for cardioversion or defibrillation purposes;

current limiting means for limiting the current that is applied to the first region of the heart when the interconnect means interconnects the first and second means wherein the current limiting means does not limit current that is applied to the first region of the heart when the second means is providing the second therapeutic stimulation pulse to the heart; and control means for providing the first or second therapeutic stimulation pulses to the heart via the first or second means and for inducing the interconnect means to interconnect the first and second means during delivery of the first therapeutic stimulation pulse to the heart and for enabling the current limited means only when the first and second means are interconnected.

12. The device of claim 11, further comprising sensing means for detecting the function of the heart wherein the control means receive a signal from the sensing means and induces the first or second means to provide the first or second therapeutic stimulation pulse in response to receiving the signal from the sense means.

13. The device of claim 12, wherein the first means comprises an RV coil that is adapted to be positioned within the right ventricle of the heart and a pectoral implant housing that is adapted to be implanted in the body of the patient that functions as the return electrode for the first therapeutic stimulation pulse.

14. The device of claim 13, wherein the second means comprises a pacing probe that is adapted to be positioned in the right ventricle of the heart in a position wherein therapeutic stimulation pulses are provided to the apex of the heart.

15. The device of claim 14, wherein the sensing means is also comprised of the pacing probe.

16. The device of claim 15, wherein the interconnect means is comprised of a circuit having one or more switches controlled by the control means that is configured to interconnect the RV coil and the pacing probe so that the pacing probe receive a portion of the energy provided to the RV coil when the RV coil is induced to provide the first therapeutic stimulation pulse.

17. The device of claim 16, wherein the circuit includes a resistor positioned in series between the first and second means so that the second means receive a current limited signal from the first means when supplying the therapeutic stimulation pulse to the apex of the heart while the first means simultaneously provides the first therapeutic stimulation pulse to the heart.

18. The device of claim 17, wherein the current limited signal is current limited to an extent sufficient to prevent damage to the pacing probe and to prevent the cardiac cells positioned adjacent the pacing probe from being stunned as a result of the pacing probe applying the therapeutic stimulation pulse stimuli to the heart.

19. The device of claim 18, wherein the peak positive current provided to the heart via the first electrode is approximately 15 amperes and the peak negative current provided to the heart via the first electrode is approximately −5 amperes and wherein the resistor limits the peak current provided by the second electrode to approximately 0.75 amperes and the peak negative current provided to the heart to approximately −0.25 amperes.

20. An implantable electrical device for applying one or more therapeutic shocks to the heart of a patient, the device comprising:
an RV coil adapted to be positioned within the right ventricle of the heart that is configured to apply a defibrillation therapeutic shock to the heart;
a pacing tip that is adapted to be positioned in the right ventricle of the heart adjacent the apex that is configured to provide pacing pulses to the apex of the heart;
an interconnect circuit that can be configured so that a portion of the energy supplied to the RV coil to apply the defibrillation therapeutic shock to the heart is supplied to the pacing tip so that the pacing probe can simultaneously provide a therapeutic shock to the apex of the heart for defibrillation purposes wherein the interconnect circuit includes a controllable switch and a current limiting resistor electrically interposed between the RV coil and the pacing tip so that, when the switch is in a first configuration, the current limiting resistor is not connected to the pacing tip and when the switch is in a second configuration the current limiting resistor is connected to the pacing tip and wherein the controllable switch is in the first configuration when the pacing tip is applying pacing pulses to the apex of the heart; and
a controller that receives a sense signal indicative of the function of the heart that induces the RV coil to produce the defibrillation shock and the pacing tip to produce the pacing pulses, wherein the controller also configures the interconnect circuit to interconnect the RV coil and the pacing probe and to induce the controllable switch into the second configuration when inducing the RV coil to produce a defibrillation shock so that a current limited therapeutic shock is simultaneously applied to the apex of the heart via the pacing tip.

21. The device of claim 20, wherein the controller is positioned within a pectoral implant can and wherein the can is configured to provide the return electrode for the defibrillation shock.

22. The device of claim 20, wherein the pacing tip provides the sense input to the controller and wherein the resistor is selected so as to limit the current that is supplied to the pacing tip so as to reduce the possibility of the cardiac cells located adjacent the pacing probe being stunned as a result of the application of the therapeutic shock.

23. The device of claim 22, wherein the resistor is comprised of a shunt resistor and wherein the interconnect circuit can also be configured by the controller to use the shunt resistor to dissipate excess stored energy through the shunt resistor.

24. A method of providing therapeutic electrical pulses to the heart through an implantable electrical device having a first electrode positioned within the ventricle that is configured to provide a first therapeutic stimulation pulse to the heart and a second electrode positioned within the ventricle of the the heart that is configured to provide a second therapeutic stimulation pulse to a first region of the heart, the method comprising the steps of:
providing the first therapeutic stimulation pulse to the heart for defibrillation or cardioversion purposes;
providing the second therapeutic stimulation pulse to the heart for pacing purposes;
interconnecting the first and second electrodes, while simultaneously providing the first therapeutic pulse to the heart so that a therapeutic stimulation pulse is simultaneously applied to the first region of the heart for cardioversion or defibrillation purposes; and
enabling a current limiting means, only during the interconnect step, so that the therapeutic stimulation pulse that is applied to the first region of the heart is current limited.

25. The method of claim 24, wherein the step of providing the first therapeutic pulse comprises inducing an RV coil positioned within the right ventricle of the heart to produce a biphasic defibrillation shock.

26. The method of claim 25, wherein the step of providing the second therapeutic pulse comprises inducing a pacing probe positioned adjacent the apex of the heart to produce a pacing pulse.

27. The method of claim 26, wherein the step of interconnecting the first and second electrodes comprises electrically interconnecting the RV coil and the pacing probe so that a current limited signal is supplied to the pacing probe which results in the therapeutic pulse being supplied to the apex of the heart simultaneously with the defibrillation shock emanating from the RV coil.

28. The method of claim 27, wherein the step of interconnecting the first and second electrodes comprises electrically connecting the RV coil and the pacing probe while interposing a shunt resistor therebetween to limit the current being supplied to the pacing probe to protect the pacing probe and to prevent the cardiac cells positioned adjacent the pacing probe from being stunned as a result of receiving the therapeutic pulse.

29. An implantable electrical device for applying stimulation pulses to the heart of a patient comprising:
a first electrode adapted to be implanted within the body of a patient and further adapted to provide cardioversion or defibrillation therapeutic stimulation pulses to the heart of the patient;
a second electrode adapted to be implanted within the body of a patient and further adapted to provide pacing stimulation pulses to the apex of the heart of the patient, wherein the second electrode is further adapted to provide current limited cardioversion or defibrillation stimulation pulses to the apex of the heart in conjunction with the first electrode providing cardioversion or defibrillation stimulation pulses to the heart;
a controllable circuit that enables the first and the second electrodes to apply the cardioversion or defibrillation stimulation pulses to the heart, wherein the controllable circuit includes a current limiting means that is engaged with the second electrode during application of the cardioversion or defibrillation therapeutic stimulation pulses so as to limit the current that is delivered to the apex of the heart; and control means for controlling the controllable circuit so as to induce the delivery of the pacing pulses and the cardioversion or defibrillation pulses, wherein the control means further controls the controllable circuit so that the current limiting means is engaged during delivery of the cardioversion or defibrillation therapeutic pulses and so that the current limiting means is disengaged during delivery of the pacing pulses.

30. The device of claim 29, wherein the control means receives an input signal indicative of the function of the heart and wherein the control means induces the first or second electrode to provide a cardioversion or defibrillation stimulation pulse or a pacing pulse to the heart based upon the input signal.

31. The device of claim 30, wherein the second electrode is comprised of a pacing probe that is adapted to be implanted into the heart tissue in an apex region of the heart and wherein the second electrode also functions as a sensor so as to provide the input signal to the heart.

32. The device of claim 31, wherein the current limiting means comprises a current limiting resistor that is connected in series between the first and second electrodes so that the portion of energy that is transmitted to the second electrode by the controllable circuit during delivery of the cardioversion or defibrillation stimulation pulse is provided to the second electrode for delivery to the apex wherein the portion of energy is current limited by the resistor so that the likelihood of damage to the second electrode and the likelihood of stunning the cardiac cells positioned adjacent the second electrode is reduced.

33. An implantable electrical device for providing therapeutic stimulation pulses to the heart, the device comprising:

a first electrode adapted to be implanted within the body of a patient and further adapted to provide cardioversion or defibrillation stimulation pulses to the heart of the patient;

a second electrode adapted to be implanted within the body of a patient and adapted to provide pacing stimulation pulses to the apex of the heart of the patient, wherein the second electrode is further adapted to provide a current limited cardioversion or defibrillation stimulation pulse to the apex of the heart in conjunction with the first electrode delivering a cardioversion or defibrillation stimulation pulse to the heart;

current limiting means for limiting the current delivered by the second electrode to the apex of the heart during delivery of cardioversion or defibrillation stimulation pulses; and control means for controlling the current limiting means and the delivery of stimulation pulses via the first and second electrode wherein the control means controls the current limiting means so that the current limiting means is engaged during delivery of cardioversion or defibrillation stimulation pulses to the apex of the heart via the second electrode and wherein the control means controls the current limiting means so that the current limiting means is disengaged during delivery of pacing pulses to the apex of the heart via the second electrode wherein the control means is capable of providing a defibrillation or cardioversion stimulation pulse to the heart of either a first or a second polarity.

34. The device of claim 33, wherein the control means receives an input signal indicative of the function of the heart and wherein the control means induces the first or second electrode to provide a cardioversion or defibrillation pulse or a pacing pulse to the heart based upon the input signal.

35. The device of claim 34, wherein the second electrode is comprised of a pacing probe that is adapted to be implanted into the heart tissue in an apex region of the heart and wherein the second electrode also functions as a sensor so as to provide the input signal to the heart.

36. The device of claim 35, wherein the current limiting means is comprised of a controllable switch and a current limiting resistor that are connected in series between the first and second electrodes so that a portion of energy provided to the first electrode is transmitted to the second electrode during delivery of the cardioversion or defibrillation stimulation pulse wherein the current limiting resistor is current limited so that the likelihood of damage to the second electrode and the likelihood of stunning the cardiac cells positioned adjacent the second electrode is reduced.

37. The device of claim 36, wherein the control means is configured to apply a biphasic defibrillation shock to the heart via the first electrode and wherein the control means includes a controllable diode bridge interposed between the current limiting resistor and the second electrode so that the circuit is configured to apply a current limited biphasic shock to the apex of the hear via the second electrode.

38. The device of claim 37, wherein the diode bridge is controllable so that the control means can apply a biphasic shock of either polarity depending upon the input signal received by the control means.

* * * * *